(12) United States Patent
Bosch I Lladó et al.

(10) Patent No.: US 8,048,876 B2
(45) Date of Patent: Nov. 1, 2011

(54) PROCESS FOR PREPARING QUETIAPINE AND QUETIAPINE FUMARATE

(75) Inventors: Jordi Bosch I Lladó, Girona (ES); Maria Carmen Burgarolas Montero, Santa Maria de Palautordera (ES); Iolanda Chamorro Gutiérrez, Santa Coloma de Farners (ES)

(73) Assignee: Medichem S.A., Barcelona (ES)

( * ) Notice: Subject to any disclaimer, the term of this patent is extended or adjusted under 35 U.S.C. 154(b) by 719 days.

(21) Appl. No.: 11/911,898

(22) PCT Filed: Apr. 21, 2006

(86) PCT No.: PCT/IB2006/002286
§ 371 (c)(1),
(2), (4) Date: Aug. 8, 2008

(87) PCT Pub. No.: WO2006/117700
PCT Pub. Date: Nov. 9, 2006

(65) Prior Publication Data
US 2009/0076262 A1    Mar. 19, 2009

Related U.S. Application Data

(60) Provisional application No. 60/673,373, filed on Apr. 21, 2005, provisional application No. 60/730,864, filed on Oct. 28, 2005.

(51) Int. Cl.
*A61P 25/08* (2006.01)
*A61K 31/554* (2006.01)
*A61K 9/14* (2006.01)
*C07D 281/16* (2006.01)

(52) U.S. Cl. .................. 514/211.13; 540/551

(58) Field of Classification Search .......... 514/211.13; 540/551
See application file for complete search history.

(56) References Cited

U.S. PATENT DOCUMENTS

| 5,286,722 A | 2/1994 | Cairns et al. |
| 2005/0003001 A1 | 1/2005 | Yamaguchi et al. |
| 2006/0063927 A1* | 3/2006 | Etlin et al. .......... 540/551 |

FOREIGN PATENT DOCUMENTS

| EP | 0 240 228 A | 10/1987 |
| WO | 01/21179 A | 3/2001 |
| WO | 02/094236 A | 11/2002 |
| WO | WO 03/080065 A1 | 10/2003 |
| WO | WO 2004078735 A1 | 9/2004 |
| WO | WO 2006/001619 A1 | 1/2006 |

OTHER PUBLICATIONS

International Search Report dated Nov. 21, 2006 for International Patent Application No. PCT/IB2006/002286.
Warawa et al. "*Behavioural Approach to Nondynskinetic Dopamine Antagonists: Identification of* Seroquel", J. Med. Chem., vol. 44, 2001, pp. 372-389.
Schmutz et al. "*29. Uber in 11-stellung amino-substitute Dibenzo[b,f]—1,4-thiazepine und—ozazepine*", Helvetica Chimica Acta, vol. 50, 1967, pp. 245-254.
Kuehne et al. "*Reduction of Amides and Lactams by Amines by Reactions with Phosphorour Oxychloride and Sodium Borohydride*", J. Org. Chem., vol. 42, No. 12, 1977, pp. 2082-2087.

* cited by examiner

*Primary Examiner* — Brenda Coleman
(74) *Attorney, Agent, or Firm* — Cozen O'Connor

(57) ABSTRACT

The invention comprises a process for preparing quetiapine and/or its salts, including, quetiapine fumarate. The process generally comprises reacting dibenzothiazepinone (dibenzo[bf][1,4]thiazepin-11(10H)-one) with phosphorous oxychloride in the presence of triethylamine in an aromatic organic solvent such as toluene or, preferably, xylene at reflux temperature to obtain an aromatic hydrocarbon solution of 11-chloro-dibenzo[bf][1,4]thiazepine. Thereafter, the 11-chloro-dibenzo[bf][1,4]thiazepine is reacted with 2-(2-piperazin-1-ylethoxy)-ethanol to yield, following several processing steps, quetiapine. Compound I can then be further reacted with fumaric acid at elevated temperature to yield quetiapine fumarate. The resulting quetiapine fumarate obtained is suitable for use in pharmaceutical preparations.

19 Claims, 1 Drawing Sheet

PROCESS FOR PREPARING QUETIAPINE AND QUETIAPINE FUMARATE

CROSS REFERENCE TO RELATED APPLICATIONS

This application claims priority under 35 U.S.C. §371 to International Application No. PCT/IB2006/002286 (filed Apr. 21, 2006), which claims priority to U.S. Provisional Application Nos. 60/673,373 (filed Apr. 21, 2005) and 60/730,864 (filed Oct. 28, 2005), all three of which applications are expressly incorporated herein by reference in their entirety.

BACKGROUND OF THE INVENTION

1. Field of the Invention

The invention relates to a process for preparing quetiapine and its salts (e.g., quetiapine fumarate). The invention further includes formulating quetiapine and/or its salts (e.g., quetiapine fumarate) (collectively, "the compounds of the invention") into readily usable dosage units for the therapeutic treatment (including prophylactic treatment) of mammals including humans.

2. Discussion of the Related Art

Quetiapine (Compound I) is the common name for 2-[2-4-Dibenzo[b,f][1,4]thiazepin-11-ylpiperazin-1-yl)ethoxy]ethanol.

Compound I

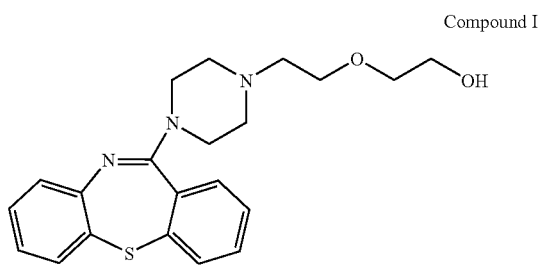

Quetiapine fumarate (Compound II) is a commercially marketed pharmaceutically active substance useful for the treatment of schizophrenia. Compound II may be made by a variety of methods.

Compound II

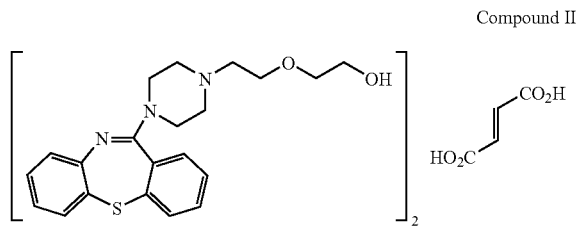

U.S. Pat. No. 4,879,288 and its equivalent EP 240 228 disclose three general processes for preparing quetiapine and quetiapine fumarate.

According to U.S. Pat. No. 4,879,288 and EP 240 228, and as illustrated in Scheme I (below), one mole of Compound III (i.e., dibenzothiazepinone, dibenzo[b,f][1,4]thiazepine-11 (10H)-one) is combined with 14.8 moles of phosphorous oxychloride and 0.6 moles of N,N-dimethylaniline and the mixture is refluxed for about 6 hours. The excess phosphorous oxychloride can then be removed under vacuum to yield a brown residue, which can then be dissolved in toluene and treated with an ice-water mixture. The toluene layer is then separated, washed twice with water and dried with anhydrous magnesium sulphate. After removal of the drying agent by filtration, the filtrate can be concentrated under vacuum to give a 92.6% yield of Compound IV (i.e., 11-chlorodibenzo [b,f][1,4]thiazepine).

Compound IV can then be combined with 2.58 L of xylene and 2 mol of Compound V (i.e., 2-(2-Piperazin-1-ylethoxy)-ethanol) and refluxed for approximately 30 hours. Thereafter, the mixture is subjected to a complex work-up, which includes using diethyl ether, in which Compound I (i.e., quetiapine) is extracted as a dichloromethanic solution. Compound I is then concentrated under vacuum to yield a viscous amber oil which is purified by flash chromatography using a silica gel column and dichloromethane as eluent. The yield of Compound I following purification is 77.7% (overall yield=71.9%).

Compound I (1 mole) is then optionally treated with 1.04 mol of fumaric acid in 3.6 mL of ethanol to yield 49.63% of Compound II (i.e., quetiapine fumarate) (overall yield of quetiapine fumarate=35.7%).

Although the process illustrated in Scheme I is feasible on an industrial scale, it is nonetheless difficult and uneconomical. Specifically, the process of Scheme I requires the use of large amounts of phosphorous oxychloride, which is both highly toxic and environmentally hazardous. Additionally, N,N-disubstituted anilines, such as N,N-dimethylaniline, are similarly dangerous and pose irreversible side effects and can be toxic to aquatic organisms. Similarly, diethyl ether and dichloromethane are toxic materials. In addition to the toxicity of some of the chemicals involved, Scheme I also requires long reaction times and the use of flash and column chromatography to obtain purified products.

Scheme I

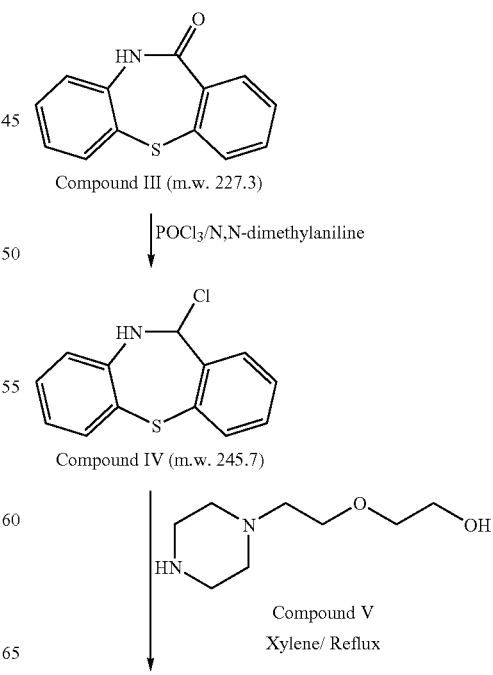

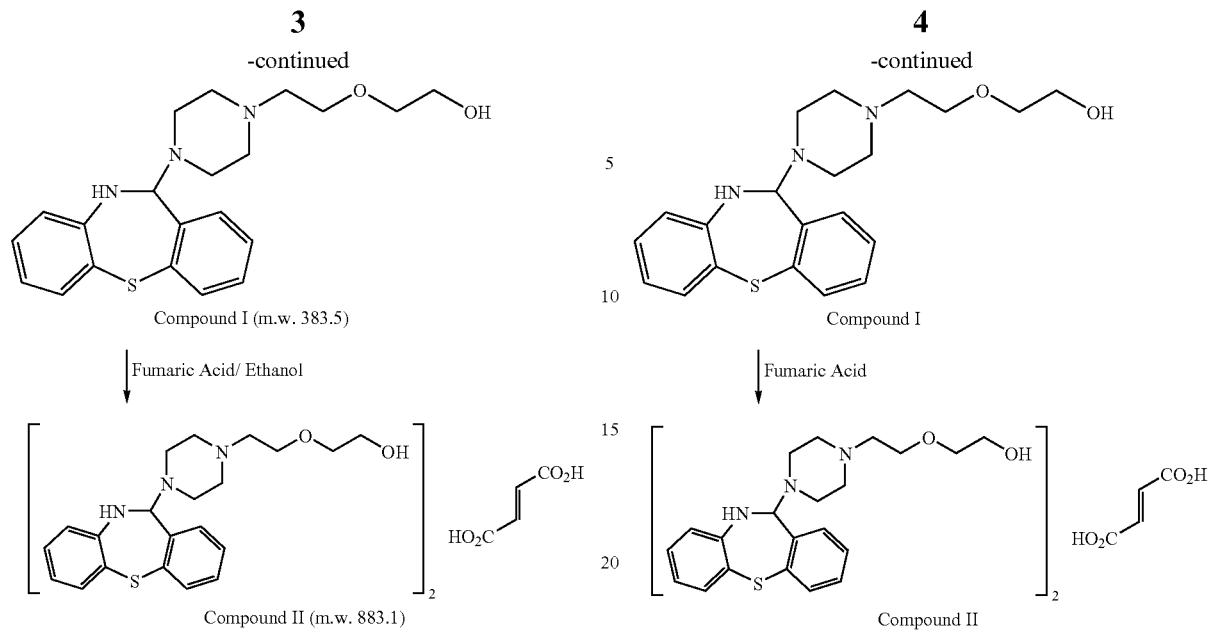

A similar process disclosed in U.S. Pat. No. 4,879,288 and EP 240 228 is illustrated in Scheme II (below) in which Compound III is converted to the corresponding thiolactam, Compound VI, followed by conversions to the corresponding thioether, Compound VII. Compound VII is then converted to Compounds I and II via reaction with Compound V.

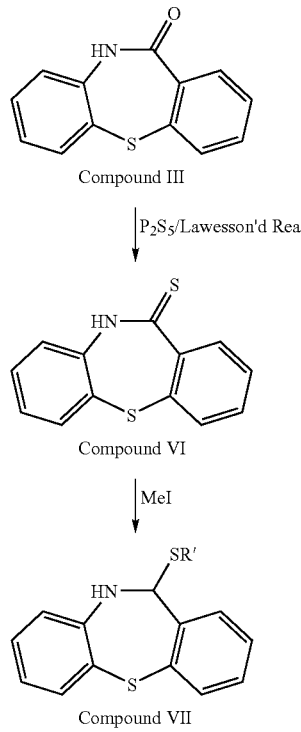

Another process disclosed in U.S. Pat. No. 4,879,288 and its equivalent EP 240 228 is illustrated in Scheme III (below).

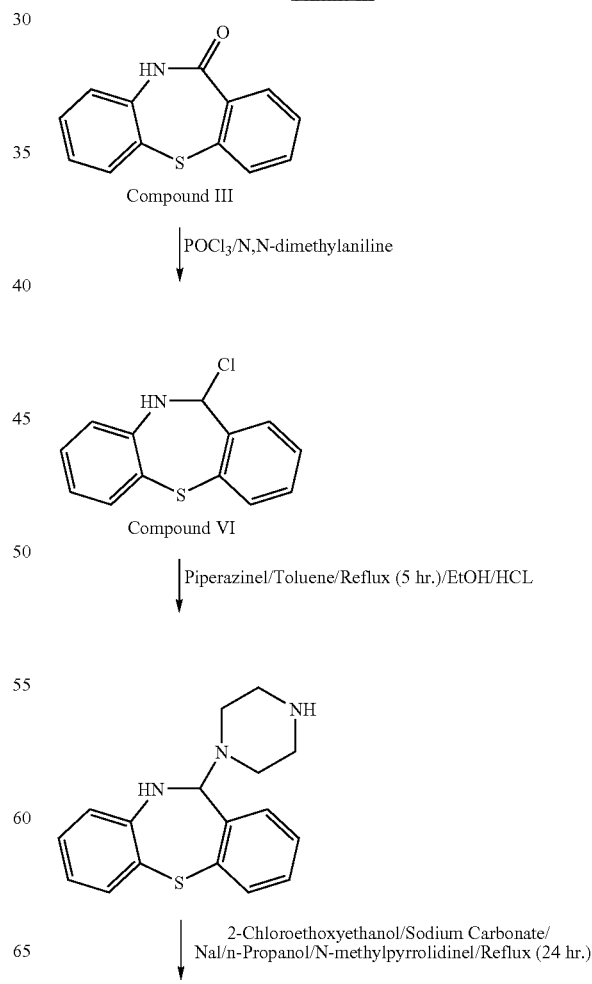

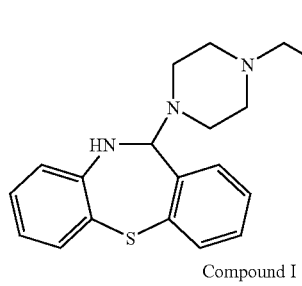

Compound I

↓ Fumaric Acid/Ethanol

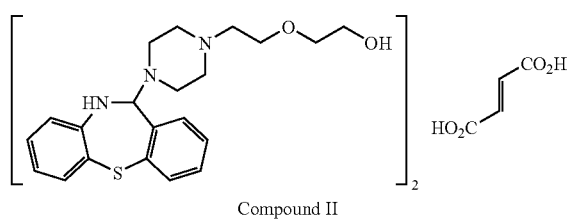

Compound II

In Scheme III, Compound III is converted to Compound IV via treatment with phosphorous oxychloride (yield=92.6%). Compound IV is then reacted with piperazine to yield 88% of Compound VIII (i.e., 11-piperazin-1-yldibenzo[b,f][1,4]thiazepine·2 HCl). Compound VIII is then reacted with 2-chloroethoxyethanol to yield Compound I (yield=78%) which is in turn readily converted to Compound II (overall yield=63.6%). A phase transfer catalyst can also be used in Scheme III (WO 2004/076431). As with Scheme I, Scheme III is both difficult and uneconomical on a large scale and, in particular, Scheme III requires the use of large quantities of phosphorous oxychloride as well as N,N-dimethylaniline (discussed above).

SUMMARY OF THE INVENTION

The invention comprises a process for preparing quetiapine (Compound I) and/or its salts, including, quetiapine fumarate (Compound II). The process generally comprises reacting Compound III (i.e., dibenzothiazepinone; dibenzo[b,f][1,4]thiazepin-11(10H)-one) with phosphorous oxychloride in the presence of triethylamine in an aromatic organic solvent such as toluene or, preferably, xylene at reflux temperature to obtain an aromatic hydrocarbon solution of Compound IV (i.e., 11-chloro-dibenzo[b,f][1,4]thiazepine). Thereafter, Compound IV is reacted with Compound V (2-(2-piperazin-1-ylethoxy)-ethanol) to yield, following several processing steps, Compound I (quetiapine; 2-[2-(4-dibenzo[b,f][1,4]thiazepin-11-ylpiperazin-1-yl)ethoxy]ethanol). If desired, Compound I can be further reacted with fumaric acid at elevated temperature to yield Compound II (quetiapine fumarate). The resulting quetiapine fumarate obtained is suitable for use in pharmaceutical preparations. These aspects of the invention are illustrated in Scheme IV (below).

Scheme IV

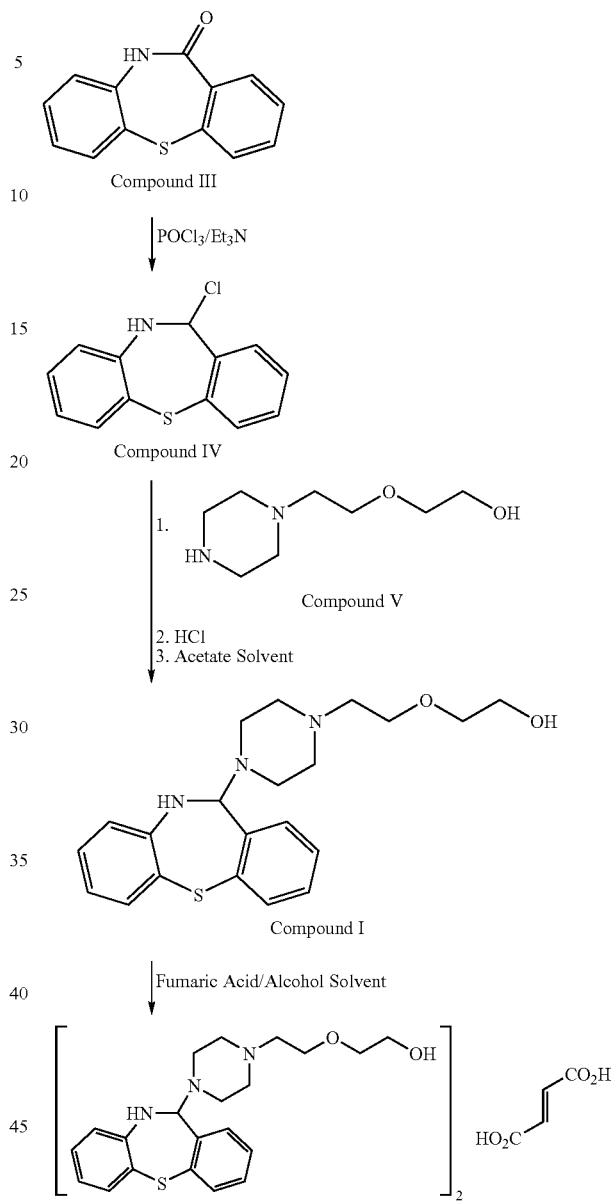

The invention further includes formulating quetiapine and/or its salts (e.g., quetiapine fumarate) into readily usable dosage units for the therapeutic treatment (including prophylactic treatment) of mammals including humans. Such formulation may include, among other things, various pharmaceutical carriers and/or diluents.

The invention provides significant improvements over the processes described in the literature for preparing quetiapine (Compound I) and/or its salts, including, quetiapine fumarate (Compound II). Namely, the invention dispenses with the need to use large quantities of phosphorous oxychloride which, as discussed above, is both highly toxic and environmentally hazardous. Additionally, phosphorous oxychloride is typically removed via distillation, a step which the present process obviates. Similarly, the process eliminates the need to use toxic N,N-disubstituted aniline compounds, including, for example, N,N-dimethylaniline. The invention further advantageously eliminates the need to isolate Compound IV and/or Compound I as solids and minimizes reaction and reflux times. The invention also minimizes and/or eliminates the need to employ hazardous solvents such as diethyl ether and dichloromethane. Moreover, the invention provides simplified means for purifying Compounds I and II (e.g., Compound I is extracted from the reaction mixture using an organic acetate solvent, preferably an alkyl acetate such as ethyl acetate or isopropyl acetate).

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION OF THE PREFERRED EMBODIMENTS

Figure 1:
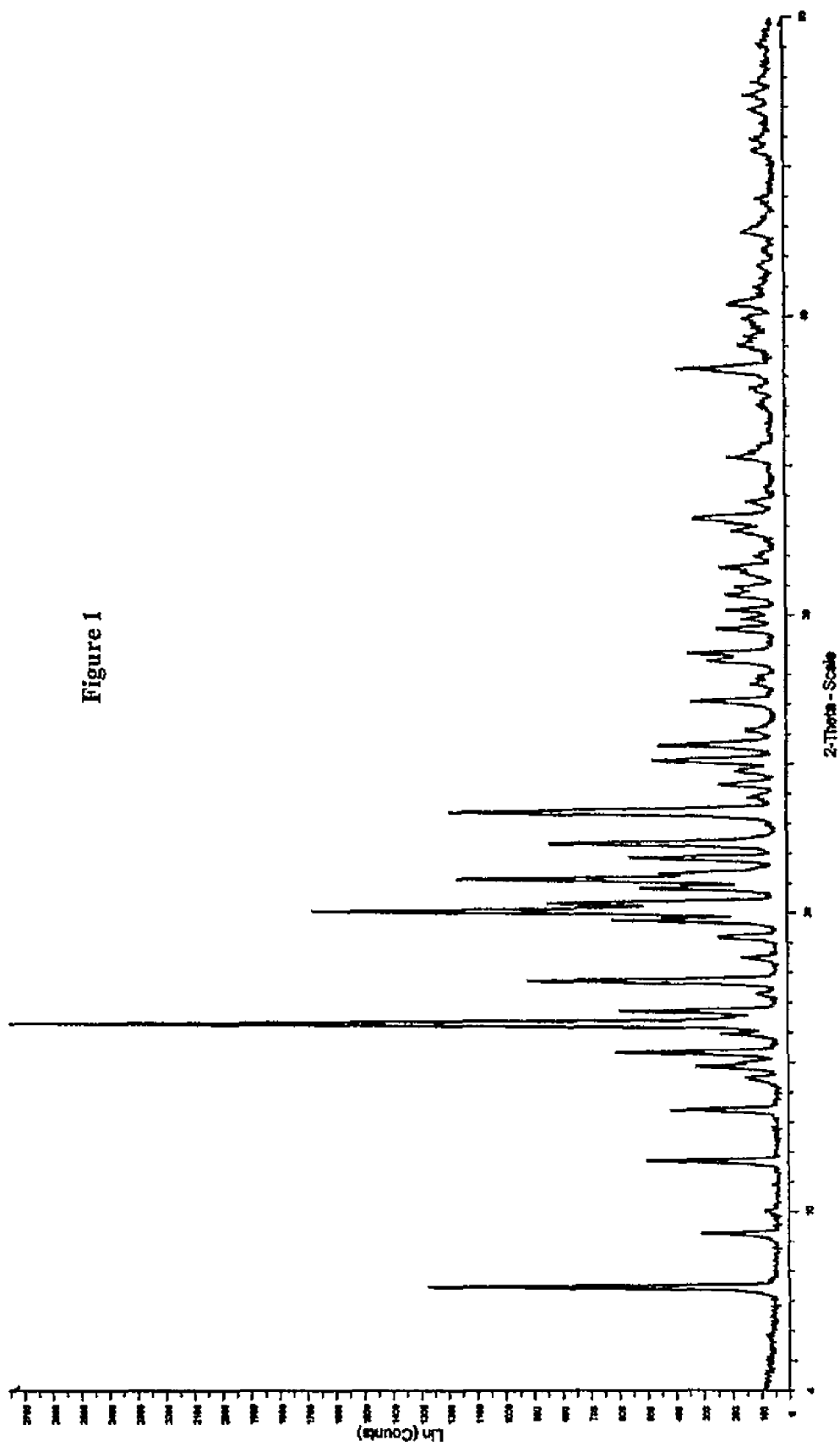
FIG. 1 illustrates the X-ray powder diffraction pattern of quetiapine fumarate (Compound II) obtained in Example 2.

Reference will now be made in detail to the preferred embodiments of the invention. This invention may, however, be embodied in many different forms and should not be construed as limited to the embodiments set forth herein. In addition, and as will be appreciated by one of skill in the art, the invention may be embodied as a method, system or process.

The invention comprises a process for preparing quetiapine (Compound I) and/or its salts, including, quetiapine fumarate (Compound II). The process generally comprises reacting Compound III (i.e., dibenzothiazepinone, Dibenzo[b,f][1,4] thiazepine-11(10H)-10 one) with phosphorous oxychloride in the presence of triethylamine in an aromatic organic solvent such as toluene (b.p. 110° C.) or, preferably, xylene (b.p. 140° C.) at reflux temperature to obtain an aromatic hydrocarbon solution of Compound IV (i.e., 11-Chloro-dibenzo[b, f][1,4]thiazepine). The molar quantity of phosphorous oxychloride used ranges between approximately 0.4 and 1.5 moles (i.e., $0.4 \leq x \leq 1.5$, wherein x is the molar quantity of phosphorous oxychloride) per mole of Compound III. Preferably the molar quantity of phosphorous oxychloride is between approximately 0.5 and 1 moles per mole of Compound III and most preferably 0.75 moles per mole of Compound III. The initial addition of the triethylamine causes a mildly exothermic reaction and gas emission. Thus, during the addition of each of the components, care should be taken to maintain the temperature of the reaction at approximately room temperature (~20-25° C.).

Once the reactants are combined, the reaction mixture was heated to reflux for at least about 1 to 6 hours, preferably from about 2 to 4 hours. After heating the reactants, the phosphorous oxychloride is destroyed in situ, for example, by the addition of water to the reaction mixture. Next, the pH of the solution was adjusted to approximately 2.5-3.5 by the addition of an aqueous alkali solution. Any alkali can be used, including, for example sodium hydroxide, potassium hydroxide, sodium carbonate, sodium bicarbonate and ammonium hydroxide. Among such alkali, sodium hydroxide is preferred. Optionally, Celite® or other filter aids can be added to the solution, which is thereafter filtered. The resulting aqueous and organic phases are then separated and the organic phase is extracted with water. Residual water in the organic phase was then removed by distillation under vacuum at a temperature not to exceed 65° C. to yield a solution of Compound IV (11-chloro-dibenzo[b,f][1,4]thiazepine).

The aromatic hydrocarbon solution of Compound IV is then combined with Compound V (2-(2-piperazin-1-ylethoxy)-ethanol) in an approximately 2:1 molar ratio of Compound V to Compound IV. The solution is then heated to reflux temperature and maintained at that temperature for at least about 1 to 8 hours, and preferably for about 6 hours. The reactor is then cooled to room temperature. Next, water and hydrochloric acid are added to the reaction mixture to form quetiapine hydrochloride. The phases are then separated, and the aqueous phase is extracted with an organic solvent such as xylene. Thereafter, the quetiapine is extracted from the aqueous solution in the form of a base by contacting the aqueous solution with an organic acetate solvent, preferably an alkyl acetate solvent such as ethyl acetate (b.p. 77° C.) or, preferably, isopropyl acetate (b.p. 88° C.) and adjusting the pH to 9-10 by the addition of an aqueous sodium hydroxide solution. The resulting aqueous and organic phases are then separated, and the aqueous phase is extracted with organic acetate solvent. Optionally, the combined organic extracts are treated with a decolorizing agent between room temperature and 60° C. The decolorizing agent can be any conventional decolorizing agent, including, but not limited to, alumina, activated alumina, silica and charcoal.

The organic acetate solvent is then removed (e.g., by distillation under vacuum) and replaced with an alcohol solvent having a $C_1$-$C_4$ chain alkyl group, such as ethanol (b.p. 78° C.) or, preferably methanol (b.p. 65° C.), to yield a solution of Compound I (i.e., quetiapine; 2-[2-(4-dibenzo[b,f][1,4]thiazepin-11-ylpiperazin-1-yl)ethoxy]ethanol). Optionally, the alcohol solution can be treated with a decolorizing agent between room temperature and 60° C. The decolorizing agent can be any conventional decolorizing agent, including, but not limited to, alumina, activated alumina, silica and charcoal.

The alcohol solution containing Compound I (quetiapine) may optionally be heated and combined with a heated solution of fumaric acid in an alcohol having a $C_1$-$C_4$ alkyl chain, such as ethanol (b.p. 78° C.) or, preferably methanol (b.p. 65° C.). After mixing the two solutions, the combined mixture is cooled and maintained for about 4 hours at approximately room temperature. The solution is then filtered to yield wet Compound II (quetiapine fumarate). The resulting product can optionally be recrystallized in an alcohol having a $C_1$-$C_4$ alkyl chain, such as ethanol (b.p. 78° C.) or preferably, methanol (b.p. 65° C.).

The resulting quetiapine fumarate obtained is suitable for use in pharmaceutical preparations.

The invention further includes quetiapine fumarate, and a process for preparing the same, of defined particle size in which the quetiapine fumarate can be produced by precipitation from appropriate solvents or by other known methods of particle size reduction (e.g., reduction of particle size starting from crystals, powder aggregates and coarse powder of quetiapine fumarate).

The invention further includes a process for preparing quetiapine fumarate of high purity.

The invention further includes a process for preparing quetiapine fumarate of high purity wherein the quetiapine fumarate is more than 99.5% pure when analyzed according to reverse phase high performance liquid chromatography (HPLC) and more preferably wherein the quetiapine fumarate is more than 99.8% pure when analyzed according to reverse phase HPLC.

The invention further includes using quetiapine fumarate of high purity in the manufacture of pharmaceutical composition.

The invention further includes formulating quetiapine and/or its salts (e.g., quetiapine fumarate) into readily usable dosage units for the therapeutic treatment (including prophylactic treatment) of mammals including humans. Such formulations are normally formulated in accordance with standard pharmaceutical practice as a pharmaceutical composition. According to this aspect of the invention, there is provided a pharmaceutical composition that comprises the compounds of the invention, as defined hereinbefore, in association with a pharmaceutically acceptable diluent or carrier.

The compositions of the invention may be in a form suitable for oral use (e.g., as tablets, fast-dissolving tablets, extended release, immediate release, lozenges, hard or soft capsules, aqueous or oily suspensions, emulsions, dispersible powders or granules, syrups or elixirs). Compositions intended for oral use may contain, for example, one or more coloring, sweetening, flavoring and/or preservative agents.

Suitable pharmaceutically-acceptable excipients for a tablet formulation include, for example, inert diluents such as lactose, sodium carbonate, calcium phosphate, calcium carbonate and different types of cellulose such as powdered cellulose or microcrystalline cellulose; granulating and disintegrating agents such as corn starch and its derivatives, crosspovidone, crosscarmellose and/or algenic acid; binding agents such as starch and pregelatinized starch; lubricating agents such as magnesium stearate, stearic acid or talc; preservative agents such as sodium benzoate, ethyl or propyl p-hydroxybenzoate; and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate, kaolin or cellulose, a disintegrating agent such as corn starch and its derivatives, crosspovidone and crosscarmellose, or as soft gelatin capsules in which the active ingredient is mixed with water or an oil such as peanut oil, liquid paraffin, olive oil or glyceryl oleate derivatives.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as the sodium salt of benzoic acid, ethyl or propyl p-hydroxybenzoate), anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the Form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The amount of a compound of this invention that is combined with one or more excipients to produce a single dosage form will necessarily vary depending upon the host treated and the particular route of administration. For example, a formulation intended for oral administration to humans may contain, for example, from 0.5 mg to 2 g of active ingredient compounded with an appropriate and convenient amount of excipients which may vary from about 5 to about 98 percent by weight of the total composition. Dosage unit forms will generally contain about 1 mg to about 500 mg of an active ingredient.

Table I illustrates a representative pharmaceutical composition (wet granulation) containing quetiapine:

TABLE 1

| Component | mg/Tablet |
|---|---|
| Quetiapine Fumarate* | 345.3 mg |
| Lactose Monohydrate | 62.1 |
| Microcrystallline Cellulose | 219.21 |
| Polyvinylpyrrolidone | 30 |
| Sodium Starch Glycolate | 54 |
| Dibasic Calcium Phosphate | 30 |
| Magnesium Stearate | 9.3 |
| Titanium Dioxide | 4.69 |
| Hydroxypropyl Methylcellulose | 11.72 |
| Polyethylene Glycol | 2.34 |
| Total | 723.36 |

*Equivalent to 300 mg of Quetiapine base.

The representative pharmaceutical composition described in Table I was prepared by mixing a portion of the microcrystalline cellulose, lactose monohydrate and sodium starch glycolate with quetiapine in a high shear mixer. These components were granulated using an aqueous polyvinylpyrrolidone solution. The obtained granules were dried in fluid bed and sieved through a 1 mm mesh. The sieved granules were then mixed with the extragranular excipients, which included the remaining part of the intragranular excipients, and the dibasic calcium phosphate in a suitable blender. Thereafter, the obtained blend was further blended with magnesium stearate. The resulting ready to press blend was compressed in a rotary tabletting machine to produce suitably sized tablets. After the compression process, the cores were film coated to give them their final appearance.

The size of the dose for therapeutic or prophylactic purposes of the compounds of the invention will naturally vary according to the nature and severity of the conditions, the age and sex of the animal or patient, and the route of administration, according to well known principles of medicine. For example, the method may comprise at least one of an hourly administration, a daily administration, a weekly administration, or a monthly administration of one or more compositions described herein.

According to the invention, suitable methods of administering the therapeutic composition of the invention to a patient include any route of in vivo administration that is suitable for delivering the composition into a patient. The preferred routes of administration will be apparent to those of skill in the art, depending on the type of condition to be prevented or treated, and/or the target cell population.

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

Specific Examples

The following examples are for illustrative purposes only and are not intended, nor should they be interpreted, to limit the scope of the invention.

General Experimental Conditions:
i. HPLC Method

Chromatographic separation was carried out in a Symmetry C8, 5 µm, 25 cm×4.6 mm I.D. column at room temperature (~20-25° C.).

The mobile phase was prepared by mixing 700 volumes of 50 mM $HClO_4$ (pH~2.5, adjusted with 50% KOH) with 300 volumes of acetonitrile. The solution was then mixed and filtered through 0.22 µm nylon filter under vacuum.

The chromatograph was equipped with a 210 nm detector and the flow rate was 1.5 mL per minute. Test samples (~20 µL) were prepared by dissolving a sufficient quantity of sample in order to obtain a 1 mg per mL concentration in the mobile phase.

ii. Particle Size Measurements and Distribution

The particle size for quetiapine fumarate was measured using a Malvern Mastersizer S particle size analyzer with an MS1 Small Volume Recirculating unit attached. A 300RF mm lens and a beam length of 2.4 mm was used. Samples for analysis were prepared by dispersing a weighed amount of quetiapine fumarate (~0.1 g) in 20 mL of toluene. The resulting suspension was sonicated for approximately 1 minute and delivered drop-wise to a background corrected measuring cell previously filled with toluene until the obscuration reached the desired level. Volume distributions were obtained for three times. Upon measurement completion, the sample cell was emptied and cleaned, refilled with suspending medium and the sampling procedure repeated again. For characterization, the values of $D_{10}$, $D_{50}$ and $D_{90}$ (by volume) were specifically listed, each one being the mean of the six values available for each characterization parameter.

iii. Method for Determining Residual Solvents

GC method: The chromatographic separation is carried out in a VOCOL capillary column of 3 µm film thickness, 1.05 m×0.53 mm i.d. column and at room temperature (20-25° C.). The chromatograph is equipped with a FID detector and a Head Space injection auxiliary device.

The oven temperature is programmed as follows: Initial 0-16 minutes, 70° C.; the temperature is then raised with a ramp rate of 25° C./minute to 150° C. and maintained at 150° C. for 3 minutes; the temperature is then raised with a ramp rate of 30° C./minute to 240° C. and maintained at 240° C. for 10 minutes.

The injector and detector temperatures are set at 220° C. and 250° C., respectively. Helium is used as carrier gas (20 psi) and a split flow of 50 mL/minute is used. Samples are heated for 30 minutes at 100° C. in the head space device. After heating, the vials are pressurized with helium (18 psi) for 0.3 minutes. The sample loop is then filled for 0.15 minutes (loop volume=1 mL) and injected for 0.5 minutes.

Procedure: The test solution is injected three times along with the standard solution of methanol and isopropyl acetate in suitable vials for head space injection. The vials are sealed with suitable crimp caps and are analyzed by headspace using the described conditions.

Standard Solutions:

Methanol: Dilute quantitatively 13 µL of methanol with 200 mL of water to obtain a solution containing 51.48 µg/mL of methanol.

Isopropyl Acetate: Dilute quantitatively 12 µL of isopropyl acetate with 200 mL of water to obtain a solution containing 52.26 µg/mL of isopropyl acetate.

Methanol and Isopropyl Acetate Mixture: Dilute quantitatively 10 mL of methanol and 1.0 mL of isopropyl acetate with 100 mL of water to obtain a solution containing 5.1 µg/mL of methanol and 0.5 µg/mL of isopropyl acetate.

Test solution: Approximately 25 mg of quetiapine accurately weighed in 5 mL of water.

Example 1

Preparation of Quetiapine Fumarate

Step 1: Formation of Compound IV
(11-chloro-dibenzo[b,f][1,4]thiazepine)

Dibenzothiazepinone (Compound III, 4.1 Kg, 18.04 mol) was combined with 19.2 Kg (22.33 L) of xylene in a suitable reactor. To the solution was added 2.07 Kg (13.50 mol, 1.26 L) of phosphorus oxychloride followed by 1.13 Kg (11.17 mol, 1.55 L) of triethylamine. The molar ratio of Compound III to phosphorous oxychloride to triethylamine to xylene is approximately 1 mol:0.7483 mol:0.6192 mol:1.2378 L. The initial addition of the triethylamine causes a mildly exothermic reaction and gas emission. Thus, during the addition of each of the components, care was taken to maintain the temperature of the reaction at approximately room temperature (~20-25° C.).

After combining the reactants, the reactor was heated to reflux (approximately 140° C.) with continuous stirring and maintained at that temperature for 4 hours. Thereafter, the reactor contents were cooled to room temperature and 6.3 Kg (6.3 L) of deionized water was added with continuous stirring. Next, 1.70 Kg (21.25 mol, 1.11 L) of 50% aqueous sodium hydroxide was added with continuous stirring to adjust the pH to approximately 2.5-3.5, followed by the addition of 0.20 Kg of Celite.® The solution was then filtered. The resulting aqueous and organic phases of the filtrate were then separated, and the organic phase was twice extracted with 2.5 Kg of deionized water. Residual water in the organic phase was then removed by distillation under vacuum at a temperature that did not exceed 65° C. The resulting organic solution was then cooled to room temperature and used in step 2.

Step 2: Formation of Compound I (2-[2-(4-dibenzo [b,f][1,4]thiazepin-11-ylpiperazin-1-yl)ethoxy]ethanol)

To the xylenic solution of Compound IV obtained in step 1 is added 6.14 Kg (35.24 mol) of 2-(2-piperazin-1-ylethoxy)-ethanol. The mixture is then heated to reflux (approximately 141° C.) and stirred at this temperature for approximately 6 hours. The molar ratio of Compound IV to Compound V is approximately 1 mol:1.95 mol.

The reactor contents were then cooled to room temperature, and 19.5 Kg of deionized water was added with continuous stirring. Next, 1.93 Kg (18.52 mol, 1.64 L) of hydrochloric acid was added with stirring to adjust the pH to approximately 4.5-5.5. The mixture was then stirred for an additional 15 minutes. Thereafter, the aqueous and organic phases were separated, and the aqueous phase was twice extracted with 4.7 Kg (5.46 L) of xylene.

The aqueous phase thus obtained was placed in a suitable reactor, and 24.7 Kg (28.36 L) of isopropyl acetate was added. The pH of the aqueous phase was then adjusted to approximately 9-10 by the addition of 3.8 Kg (47.5 mol, 2.48 L) of an aqueous sodium hydroxide solution (e.g., 50% aqueous sodium hydroxide solution). The phases were then separated, and the aqueous phase was extracted with 6.4 Kg (7.35 L) of isopropyl acetate. Next, the combined organic extracts were treated with active charcoal at room temperature for approximately 1 hour and filtered.

The isopropyl acetate was removed by distillation under vacuum to a final volume of approximately 15 L without exceeding a temperature of approximately 60° C. The isopropyl acetate was further removed by adding 21 Kg (26.51 L) of methanol and continuing the distillation under vacuum to a final volume of approximately 15 L without exceeding a temperature of approximately 60° C. Next, 13.5 Kg (17.04 L) of methanol was added, and the reactor contents were cooled to room temperature. The resulting organic solution of 2-[2-(4-dibenzo[b,f][1,4]thiazepin-11-ylpiperazin-1-yl)ethoxy] ethanol was then filtered, and a sample was titrated to assay the content of 2-[2-(4-dibenzo[b,f][1,4]thiazepin-11-ylpiperazin-1-yl)ethoxy]ethanol.

Step 3: Formation of Compound II (2-[2-(4-dibenzo [b,f][1,4]thiazepin-11-ylpiperazin-1-yl)ethoxy]ethanol Fumarate)

The organic solution containing 5.39 Kg (14.06 mol) of Compound I obtained in step 2 was heated to approximately 50-55° C. Separately, 0.82 Kg of fumaric acid (7.06 mol) and 8.1 Kg (10.23 L) of methanol were combined in a suitable reactor and were heated to approximately 50-55° C. and maintained at this temperature with continuous stirring for approximately 15 minutes. The heated fumaric acid solution was then poured into the solution containing Compound I while maintaining the temperature at approximately 50-55° C. The mixture was maintained at 50-55° C. for approximately 30 minutes with continuous stirring. The reactor was then cooled to room temperature and maintained at 20-25° C. for approximately 5 hours and 20 minutes.

Thereafter, the suspension was filtered, and the collected wet solid was dried under vacuum at 60° C. until constant weight to yield 5.7 Kg (12.91 mol, 91.85%) of quetiapine fumarate. The solid was then milled and sieved through a 500 µm screen and blended for 2 hours.

Analytical data: HPLC purity: 99.72%; Residual solvents (as determined by gas chromatography): isopropyl acetate<100 ppm and methanol 903.15 ppm; Particle size: ~10% by volume of the particles have a diameter below ~4.61 µm, ~50% by volume of the particles have a diameter below ~16.60 µm, ~90% by volume of the particles have a diameter below ~33.70 µm; Titration 99.26%.

Example 2

Preparation of Quetiapine Fumarate

Step 1: Formation of Compound IV (11-chloro-dibenzo[b,f][1,4]thiazepine)

Dibenzothiazepinone (Compound III, 100 g, 0.440 mol) was combined with 600 mL of xylene in 2 L flask kept at room temperature under a nitrogen atmosphere. To the solution was added 50.60 g (0.330 mol, 30.82 mL) of phosphorus oxychloride followed by 27.60 g (0.273 mol, 37.81 mL) of triethylamine. The molar ratio of Compound III to phosphorous oxychloride to triethylamine to xylene is 1 mol:0.75 mol: 0.6205 mol:1.363 L. The initial addition of the triethylamine causes a mildly exothermic reaction and gas emission. Thus, during the addition of each of the components, care was taken to maintain the temperature of the reaction at approximately room temperature (~20-25° C.).

After combining the reactants, the resulting white suspension was heated to approximately 140° C. with continuous stirring and maintained at that temperature for approximately 9.5 hours. Thereafter, the reactor contents were cooled to room temperature and 154 g (154 mL) of deionized water was added with continuous stirring for approximately 30 minutes. Next, 35.19 g (0.44 mol, 23 mL) of 50% aqueous sodium hydroxide was added with continuous stirring to adjust the pH to approximately 2.5-3.5, followed by the addition of 5 g of Celite.® The solution was then filtered. The resulting aqueous and organic phases of the filtrate were then separated, and the organic phase was twice extracted with 61 g (61 mL) of deionized water. Residual water in the organic phase was then removed by distillation under vacuum at a temperature that did not exceed 65° C. The resulting organic solution was then cooled to room temperature and used in step 2.

Step 2: Formation of Compound I (2-[2-(4-dibenzo [b,f][1,4]thiazepin-11-ylpiperazin-1-yl)ethoxy]ethanol)

To the xylenic solution of Compound IV obtained in step 1 is added 149.78 g (0.86 mol) of 2-(2-piperazin-1-ylethoxy)-ethanol. The mixture was then heated to reflux (approximately 141° C.) under nitrogen and stirred at this temperature for approximately 6 hours. The molar ratio of Compound IV to Compound V is approximately 1:2.16.

The reactor contents were then cooled down to room temperature and 476.02 g (476.02 mL) of deionized water was added with continuous stirring. The addition of water causes a mildly exothermic reaction and gas emission. Next, 47 g (0.45 mol, 40 mL) of hydrochloric acid was added to adjust the pH to approximately 4.5-5.5 with stirring. The mixture was then stirred for an additional 30 minutes. Thereafter, the aqueous and organic phases were separated, and the aqueous phase was twice extracted with 114.08 g (132.65 mL) of xylene.

The aqueous phase thus obtained was placed in a suitable reactor, and 602.37 g (691.58 mL) of isopropyl acetate was added. The pH of the aqueous phase was then adjusted to approximately 9-10 by the addition of 30.06 g (0.38 mol, 46 mL) of a 50% aqueous sodium hydroxide solution. The phases were then separated, and the aqueous phase was extracted with 155.21 g (178.20 mL) of isopropyl acetate and stirred for 30 minutes. Next, the combined organic extracts were treated with activated charcoal at room temperature for approximately 1 hour and filtered.

The isopropyl acetate was then removed by distillation under vacuum using a temperature that did not exceed approximately 60° C. to yield an oily residue. The isopropyl acetate was further removed by adding 120 g (151.51 mL) of methanol and continuing the distillation under vacuum without exceeding a temperature of approximately 60° C. The resulting oily residue of 2-[2-(4-dibenzo[b,f][1,4]thiazepin-11-ylpiperazin-1-yl)ethoxy]ethanol was sampled and titrated to assay the content of 2-[2-(4-dibenzo[b,f][1,4]thiazepin-11-ylpiperazin-1-yl)ethoxy]ethanol and then dissolved in 546 g (689.39 mL) of methanol to obtain a pale orange solution.

Step 3: Formation of Compound II (2-[2-(4-dibenzo [b,f][1,4]thiazepin-11-ylpiperazin-1-yl)ethoxy]ethanol Fumarate)

The organic solution containing 142 g (0.37 mol) of Compound I obtained in step 2 was heated to approximately 50-55° C. Separately, 21.60 g (0.19 mol) of fumaric acid and 194.4 g (245.45 mL) of methanol were combined in a suitable reactor and were heated to approximately 50-55° C. The heated fumaric acid solution was then poured into the solution containing Compound I while maintaining the temperature at approximately 50-55° C. The ratio of Compound I to fumaric acid was approximately 1 mol:0.51 mol. The reactor was then cooled to room temperature and maintained at 20-25° C. for approximately 4 hours.

Thereafter, the suspension was filtered, and the collected wet solid was dried under vacuum at 60° C. until constant weight to yield 147.66 g (0.33 mol, 90.73%) of quetiapine fumarate.

Analytical data: HPLC purity: 99.73%; Residual solvents (as determined by gas chromatography): isopropyl acetate<100 ppm and methanol 122 ppm; Titration: 99.97%; RD (2 θ), see FIG. 1.

Example 3

Preparation of Quetiapine Fumarate

Step 1: Formation of Compound IV (11-chloro-dibenzo[b,f][1,4]thiazepine)

Dibenzothiazepinone (Compound III, 4.1 Kg, 18.04 mol) was combined with 19.2 Kg (22.33 L) of xylene in a suitable reactor. To the solution was added 2.07 Kg (13.50 mol, 1.26 L) of phosphorus oxychloride followed by 1.13 Kg (11.17 mol, 1.55 L) of triethylamine. The molar ratio of Compound III to phosphorous oxychloride to triethylamine to xylene is approximately 1 mol:0.7483 mol:0.6192 mol: 1.2378 L. The initial addition of the triethylamine causes a mildly exothermic reaction and gas emission. Thus, during the addition of each of the components, care was taken to maintain the temperature of the reaction at approximately room temperature (~20-25° C.).

After combining the reactants, the reactor was heated to reflux (approximately 140° C.) with continuous stirring and maintained at that temperature for 4 hours. Thereafter, the reactor contents were cooled to room temperature and 6.3 Kg (6.3 L) of deionized water was added with continuous stirring. Next, 1.40 Kg (17.5 mol, 0.9 L) of 50% aqueous sodium hydroxide was added with continuous stirring to adjust the pH to approximately 2.5-3.5, in this case 3.2, followed by the addition of 0.20 Kg of Celite.® The solution was then stirred for about 25 minutes and filtered. The resulting aqueous and organic phases of the filtrate were then separated, and the organic phase was twice extracted with 2.5 Kg of deionized water. Residual water in the organic phase was then removed by distillation under vacuum at a temperature that did not exceed 65° C. The resulting organic solution was then cooled to room temperature and used in step 2.

Step 2: Formation of Compound I (2-[2-(4-dibenzo [b,f][1,4]thiazepin-11-ylpiperazin-1-yl)ethoxy]ethanol)

To the xylenic solution of Compound IV obtained in step 1 is added 6.14 Kg (35.24 mol) of 2-(2-piperazin-1-ylethoxy)-ethanol. The mixture is then heated to reflux (approximately 141° C.) and stirred at this temperature for approximately 6 hours. The molar ratio of Compound IV to Compound V is approximately 1 mol: 1.95 mol.

The reactor contents were then cooled to room temperature, and 19.5 Kg of deionized water was added with continuous stirring. Next, 1.89 Kg (18.14 mol, 1.61 L) of hydrochloric acid was added with stirring to adjust the pH to approximately 4.5-5.5, in this case 5.3, and the mixture was then stirred for an additional 15 minutes. Thereafter, the aqueous and organic phases were separated, and the aqueous phase was twice extracted with 4.7 Kg (5.46 L) of xylene.

The aqueous phase thus obtained was placed in a suitable reactor, and 24.7 Kg (28.36 L) of isopropyl acetate was added. The pH of the aqueous phase was then adjusted to approximately 9-10 by the addition of 2.4 Kg (30 mol, 1.57 L) of an aqueous sodium hydroxide solution. The phases were then separated, and the aqueous phase was extracted with 6.4 Kg (7.35 L) of isopropyl acetate. Next, the combined organic extracts were treated with 66 g of active charcoal at room temperature for approximately 1 hour and filtered.

The isopropyl acetate was removed by distillation under vacuum without exceeding a temperature of approximately 60° C. The isopropyl acetate was further removed by adding 10.3 Kg (8.2 L) of methanol and continuing the distillation under vacuum without exceeding a temperature of approximately 60° C. Next, 21.1 Kg (26.6 L) of methanol was added, and the reactor contents were cooled to room temperature. The resulting organic solution of 2-[2-(4-dibenzo[b,f][1,4]thiazepin-11-ylpiperazin-1-yl)ethoxy]ethanol was then filtered, and a sample was titrated to assay the content of 2-[2-(4-dibenzo[b,f][1,4]thiazepin-11-ylpiperazin-1-yl)ethoxy]ethanol.

Step 3: Formation of Compound II (2-[2-(4-dibenzo [b,f][1,4]thiazepin-11-ylpiperazin-1-yl)ethoxy]ethanol Fumarate)

Fumaric acid (0.93 Kg, 8.01 mol) was combined with 8 Kg (10.10 L) of methanol in a suitable reactor and were heated to approximately 50-55° C. and maintained at this temperature with continuous stirring for approximately 15 minutes. The heated fumaric acid solution was then poured into the solution containing Compound I obtained in step 2 at room temperature (6.14 Kg; 16.01 mol of Compound I). The reactor was then cooled to room temperature and maintained at 20-25° C. for approximately 6 hours and 15 minutes.

Thereafter, the suspension was filtered, and the collected wet solid were combined with 14 Kg (17.67 L) of methanol. The mixture was then heated to reflux (approximately 66° C.) and stirred at this temperature for 2 hours. Next, the reactor was cooled to room temperature and maintained at 20-25° C. for a minimum of 1 hour. The suspension was then filtered, and the collected wet solid was dried under vacuum at 60° C. until constant weight to yield 6.12 Kg (13.86 mol, 86.54%) of quetiapine fumarate. The solid was then milled and sieved through a 500 µm screen and blended for 2 hours.

Analytical data: HPLC purity: 99.91%; Residual solvents (as determined by gas chromatography): isopropyl acetate<100 ppm and methanol 593 ppm; Particle size data: ~10% by volume of the particles have a diameter below ~3.3 µm, ~50% by volume of the particles have a diameter below ~15.4 µm and ~90% by volume of the particles have a diameter below ~33.4 µm; Titration: 100.37%.

Example 4

Preparation of Quetiapine Fumarate

Steps 1-3: Same as Example 1

Analytical data: Particle size: ~10% by volume of the particles have a diameter below ~3.5 µm, ~50% by volume of the particles have a diameter below ~12.3 µm, ~90% by volume of the particles have a diameter below ~34.4 µm.

What is claimed is:

1. A process for preparing quetiapine (Compound I) comprising:
   i. reacting dibenzothiazepinone (Compound III) with phosphorous oxychloride and an organic amine to yield 11-chlorodibenzo[b,f][1,4]thiazepine (Compound IV);
   ii. destroying the phosphorous oxychloride in situ; and
   iii. reacting Compound IV with 2-(2-piperazin-1-ylethoxy)-ethanol (Compound V) to yield Compound I.

2. The process of claim 1, wherein said organic amine is triethylamine.

3. The process of claim 1 further comprising isolating Compound I by extracting Compound I using a first organic solvent.

4. The process of claim 1 further comprising converting Compound I into quetiapine fumarate (Compound II).

5. The process of claim 3, wherein said first organic solvent is an organic acetate solvent.

6. The process of claim 5, wherein said first organic solvent is at least one of isopropyl acetate, ethyl acetate and combinations thereof.

7. The process of claim 1, further comprising iv. reacting Compound I with fumaric acid in an alcohol solvent to yield quetiapine fumarate (Compound II).

8. The process of claim 7 further comprising treating at least one of Compound I and Compound II with a decolorizing agent.

9. The process of claim 7 further comprising recrystallizing at least one of Compound I and Compound II with a second organic solvent.

10. The process of claim 9, wherein said second organic solvent is an alcohol solvent.

11. The process of paragraph 10, wherein said alcohol solvent is at least one of an alcohol having a C1-C4 alkyl chain and combinations thereof.

12. The process of claim 11, wherein said alcohol is at least one of methanol, ethanol and combinations thereof.

13. The process of claim 7, wherein said phosphorous oxychloride is present in a molar range of approximately 0.4:1 to approximately 1.5:1 relative to Compound III.

14. The process of claim 13, wherein said phosphorous oxychloride is present in a molar range of approximately 0.5:1 to approximately 1:1 relative to Compound III.

15. The process of claim 14, wherein said phosphorous oxychloride is present in a molar range of approximately 0.75:1 relative to Compound III.

16. The process of claim 1, wherein said phosphorous oxychloride is present in a molar range of approximately 0.4:1 to approximately 1.5:1 relative to Compound III.

17. The process of claim 16, wherein said phosphorous oxychloride is present in a molar range of approximately 0.5:1 to approximately 1:1 relative to Compound III.

18. The process of claim 17, wherein said phosphorous oxychloride is present in a molar range of approximately 0.75:1 relative to Compound III.

19. The process of claim 16, wherein said organic amine is triethylamine.

* * * * *